(12) United States Patent
Carpentier et al.

(10) Patent No.: US 8,862,244 B2
(45) Date of Patent: Oct. 14, 2014

(54) INTRACEREBRAL ELECTRODE

(75) Inventors: Alexandre Carpentier, Paris (FR);
Christophe Boillon, Pouligney (FR)

(73) Assignees: Assistance Publique-Hopitaux de Paris Etablissement Public, Paris (FR); Dixi Microtechniques Societe Par Actions Simplifiee, Besancon (FR)

( * ) Notice: Subject to any disclaimer, the term of this patent is extended or adjusted under 35 U.S.C. 154(b) by 0 days.

(21) Appl. No.: 13/522,569

(22) PCT Filed: Jan. 24, 2011

(86) PCT No.: PCT/FR2011/000044
§ 371 (c)(1),
(2), (4) Date: Jul. 17, 2012

(87) PCT Pub. No.: WO2011/089342
PCT Pub. Date: Jul. 28, 2011

(65) Prior Publication Data
US 2012/0296404 A1    Nov. 22, 2012

(30) Foreign Application Priority Data
Jan. 25, 2010   (FR) ..................... 10 50450

(51) Int. Cl.
*A61N 1/05* (2006.01)
*A61B 5/0478* (2006.01)
*A61B 18/00* (2006.01)

(52) U.S. Cl.
CPC ..... *A61B 5/0478* (2013.01); *A61B 2018/00023* (2013.01); *A61N 1/0534* (2013.01)
USPC ........................... 607/116; 606/41

(58) Field of Classification Search
USPC ......................................... 607/116
See application file for complete search history.

(56) References Cited

U.S. PATENT DOCUMENTS

| | | | |
|---|---|---|---|
| 5,843,150 A | 12/1998 | Dreessen et al. | |
| 5,913,854 A * | 6/1999 | Maguire et al. | 606/41 |
| 6,682,508 B1 | 1/2004 | Meythaler et al. | |
| 6,939,350 B2 * | 9/2005 | Phan | 606/49 |
| 2004/0010208 A1 | 1/2004 | Ayad | |
| 2004/0082984 A1 | 4/2004 | Osorio et al. | |
| 2004/0215162 A1 * | 10/2004 | Putz | 604/500 |

(Continued)

FOREIGN PATENT DOCUMENTS

| | | | |
|---|---|---|---|
| WO | 2007/020363 A1 | 2/2007 | |
| WO | 2007/061982 A1 | 5/2007 | |

*Primary Examiner* — Carl H Layno
*Assistant Examiner* — Erin Piateski
(74) *Attorney, Agent, or Firm* — Davis & Bujold, PLLC; Michael J. Bujold

(57) ABSTRACT

An intracerebral electrode (11) which includes a narrow elongated body (1) for being implanted in a patient's brain. The body has contact pads (2) that are electrically connected to a measuring apparatus, and a mounting member (4) for attachment to the body to the patient's head. The electrode body has a closed distal end (5) and is hollow for receiving a treatment instrument (6). The intracerebral electrode (11) comprises a closed inner fluid flow circuit (20) formed inside the body (1) of the electrode to an area adjacent the closed distal end (5), and a connection mechanism (7) located outside the body which connects the closed inner fluid flow circuit to an outer fluid flow circuit so that fluid, flowing through the outer fluid flow circuit, flows into the electrode through the inner fluid flow circuit and controls the temperature of the electrode (11).

20 Claims, 2 Drawing Sheets

(56) References Cited

U.S. PATENT DOCUMENTS

| | | | |
|---|---|---|---|
| 2005/0090880 A1* | 4/2005 | Venturelli | 607/99 |
| 2006/0212026 A1* | 9/2006 | Abboud et al. | 606/20 |
| 2009/0005843 A1* | 1/2009 | Smyth | 607/113 |
| 2010/0168826 A1 | 7/2010 | Carpentier | |

* cited by examiner

INTRACEREBRAL ELECTRODE

This application is a National Stage completion of PCT/FR2011/000044 filed Jan. 24, 2011, which claims priority from French patent application serial no. 10/50450 filed Jan. 25, 2010.

Technical Scope:

The present invention relates to an intracerebral electrode including a narrow, elongated body that is intended to be implanted in the brain of a patient, said body being provided with contact pads that are electrically connected to a measuring apparatus, and a mounting member that is set up so as to attach said body to the head of the patient, said electrode body being hollow in order to receive a treatment instrument and being provided with a closed distal end.

Prior Technique:

These intracerebral electrodes are connected to a measuring apparatus of the type of an electro-encephalogram and are widely used to detect areas to be treated in the brain, in particular dysfunction areas responsible for neurologic or psychiatric symptoms. These electrodes are increasingly used in combination with other treatment instruments in order to detect the area to be treated and carry out the treatment almost simultaneously, without having to remove the electrode, which allows targeting the treated area with great accuracy. An example is illustrated in publication US 2004/0215162, allowing sending a treatment fluid or removing a part of the cerebral fluid through a catheter inserted in a hollow intracerebral electrode and the distal end of which is open for the passage of the catheter. A similar example is illustrated in publication U.S. Pat. No. 5,843,150. Another example, described in publication US 2004/0082984, relates to an intracerebral electrode allowing treating certain areas of the brain with an appropriately refrigerated fluid. This fluid flows in a loop between an external tank and the electrode inside of which it flows, passing first through a central tube, and then through a peripheral channel before it returns in said tank. Such an electrode however does not allow treating jointly an affected area with an additional treatment instrument introduced inside or the electrode. Moreover, document WO 2007/061982 teaches the possibility of performing an ablation of an area of the brain at the same time as a record of brain activity, by means of an electrode implanted in the brain through the venous system. Again, no protection system for the areas surrounding the treated area is provided.

Another example is illustrated in publication WO 2007/020363, which allows performing a thermolesion with a laser beam or by cryogenics, the treatment instrument (fiber optic or similar) being mounted in a hollow intracerebral electrode provided with a side window transparent to radiations. This kind of treatment is for example used for treating an epileptogenic focus at the level of the hippocampus. However, the application of the heat or cold source must be targeted, controlled and mastered very accurately in order not to destroy the surrounding cerebral areas by necrosis, to respect the healthy cerebral areas as well as the intracranial arteries. In particular, the release of heat or cold produced by the treatment instrument can damage irreversibly the tissues around the deliberately treated area by conduction through the intracerebral electrode. A too important release of heat or cold might also impair the operation of the intracerebral electrode and might even lead to its destruction. Special attention must be paid when stopping the treatment, since the contact pads dissipate the accumulated thermal energy very slowly. These contact pads must have specific characteristics, allowing to achieve the best image possible when monitoring with a magnetic resonance imaging (MRI) system.

DESCRIPTION OF THE INVENTION

The present invention aims to solve this problem by suggesting to associate thermal regulation means with a specific intracerebral electrode in order to eliminate any risk of irradiation, irrespective of its source, of the areas of the brain located on the periphery of the treated area.

To that purpose, the invention relates to an intracerebral electrode of the kind stated in the preamble, characterized in that said electrode comprises a closed inner fluid flow circuit provided inside said electrode body up to an area near said closed distal end, and connection means located outside said body so as to connect said closed inner fluid flow circuit to an outer fluid flow circuit so that said fluid, moved through said outer fluid flow circuit, flows into said electrode through said inner fluid flow circuit.

Thanks to this inner fluid flow, it is possible to control and master the dissipation of heat or cold by the electrode and to prevent any collateral damage due to a treatment with the help of an instrument such as for example a fiber optic, introduced in the hollow body of the electrode. In effect, this fluid flow allows limiting the thermal capacitance of the treated tissue by cooling it down during and immediately after the treatment in order to prevent a thermal spread to the neighboring healthy tissues. Furthermore, the cooling allows preventing any phenomena of bubbling, that is to say of creation of air bubbles (pop-corn effect) which pose a risk of induced bleeding and a risk of an artifact on the MRI images. Finally, this cooling allows avoiding any phenomena of carbonization of the treated tissue due to the contact with the probe and hence avoiding the creation of an adherence of the probe to the treated tissue.

In a preferred embodiment, said inner fluid flow circuit comprises a hollow tube that delimits a central channel provided with at least one inlet opening and one outlet opening, the wall of this tube is a double wall that delimits at least one peripheral channel provided with at least one inlet opening and one outlet opening, said connection means comprise the inlet opening of one of the channels and the outlet opening of the other channel, and said channels communicate with each other through the outlet opening of one of the channels and the inlet opening of the other channel.

In a first embodiment variant, said tube forms the body of said electrode, while in a second embodiment variant, it forms a separate part accommodated in the hollow body of said electrode.

The tube can comprise at least two peripheral channels, one of the channels belonging to the fluid flow means while the other channel delimits a sealed and insulated passage for the electrical power supply wires of the contact pads.

Said electrode body and/or said tube are advantageously made out of materials permeable to magnetic radiation. They may also be made out of materials permeable to laser radiation.

The electrode comprises preferably a plug arranged to close said body and/or said tube in a tight manner, under vacuum or not.

The electrode may comprise at least one side window transparent to laser radiation near its distal end, and said contact pads may be glued or overmolded on said electrode body. In another embodiment variant, the contact pads and/or the electrical wires may be formed by vacuum deposition of metal.

BRIEF DESCRIPTION OF THE DRAWINGS

The present invention and its advantages will be better revealed in the following description of two embodiments given as non limiting examples, in reference to the drawings in appendix, in which.

ILLUSTRATIONS OF THE INVENTION AND DIFFERENT WAYS OF REALIZING IT

Figure 1:
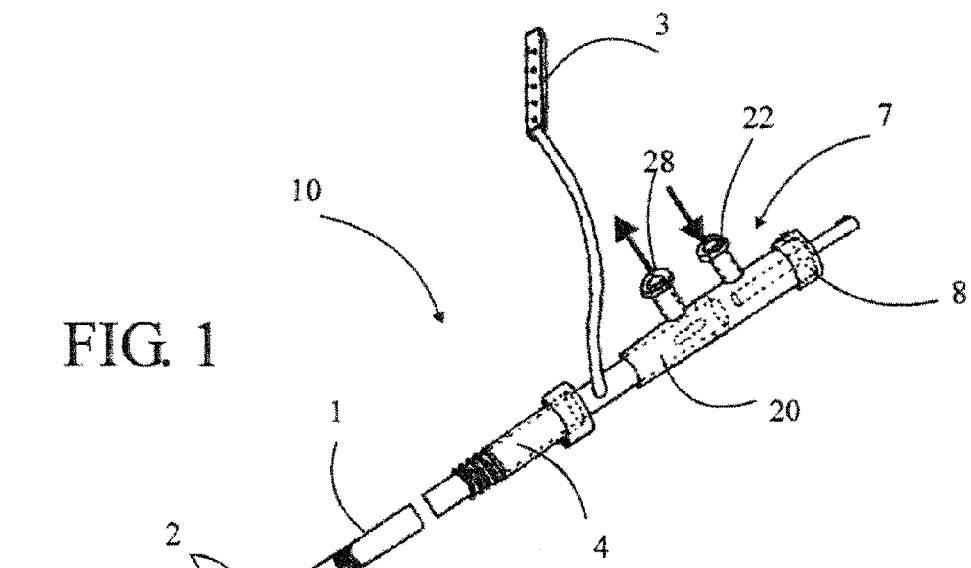
FIG. 1 is a side view of an intracerebral electrode according to the invention, in one part.

Referring to FIG. 1, the intracerebral electrode 10 according to the invention comprises a narrow, elongated body 1 that is intended to be implanted in the brain of a patient, this body being provided with contact pads 2 that are electrically connected to a measuring apparatus such as an electro-encephalogram (not represented) by means of a multi-contact connector 3. It comprises a mounting member 4 with a screw or similar, set up so as to attach the body 1 of the electrode 10 to the head of the patient. The body 1 of the electrode is hollow in order to receive a (not represented) treatment instrument and provided with a closed distal end 5. Depending on the type of operation, the treatment instrument introduced in the intracerebral electrode 10 may be a heat generator such as a fiber optic 6 (refer to FIGS. 3A and 3B) generating a laser beam, a cryogenic cold generator, or a similar device in order to create for example a thermolesion of the targeted cerebral area. Of course, these examples are not limitative.

Figure 3A:
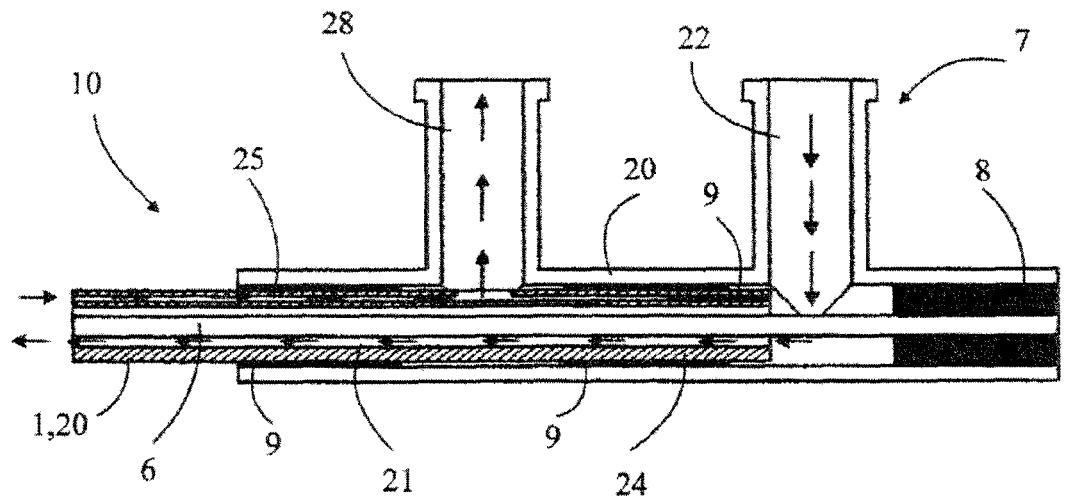
FIGS. 3A and 3B are axial cross-sectional views of the electrode of FIG. 1, respectively of its upper section and of its lower section.
Figure 3B:
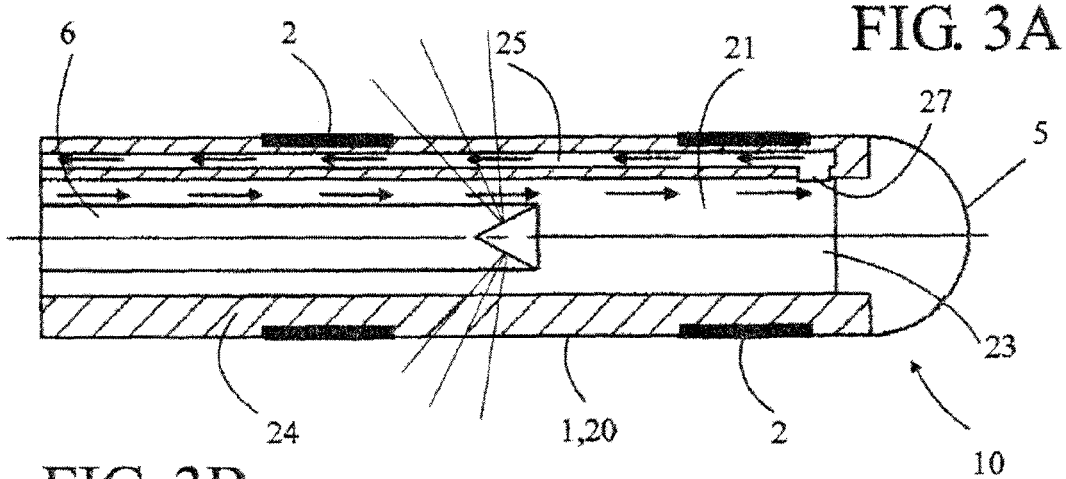
Figure 4:
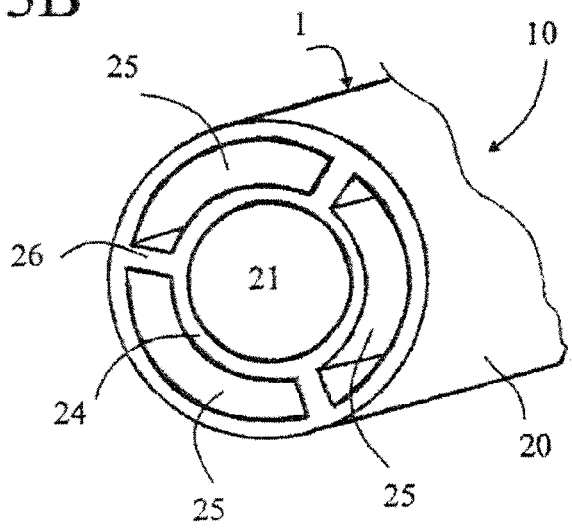
FIG. 4 is a radial cross-sectional view of the electrode of FIG. 1.

Referring more specifically to FIGS. 3A, 3B and 4, this intracerebral electrode 10 is completed with a closed inner fluid flow circuit provided inside the body 1 up to an area near the closed distal end, and connection means 7 located outside said body 1 so as to connect the closed inner fluid flow circuit to an outer fluid flow circuit (not represented) so that the fluid, moved through the outer fluid flow circuit, flows into the electrode 10 through the inner fluid flow circuit.

The fluid used may be a physiological liquid or any other suitable fluid able to transport heat or cold, in order to regulate thermally the electrode according to a predetermined temperature set point, controlled by the outer fluid flow circuit and driven by a pump able to vary the fluid flow or by any equivalent system.

The inner fluid flow circuit comprises a hollow tube 20 that delimits a central channel 21 provided with at least one proximal inlet opening 22 and one distal outlet opening 23 near the distal end 5 of the electrode 10. The wall of this tube comprises a double wall 24 that delimits at least one peripheral channel 25, and, in the example, three channels distributed on the periphery and separated from each other by a radial wall 26, these channels may have the same cross-section or not. At least one of these channels 25 comprises at least one distal inlet opening 27 near the distal end 5 of the electrode 10 and communicating with the outlet opening 23 of the central channel 21, and a proximal outlet opening 28. In the example shown, the inlet opening 22 of the central channel 21 and the outlet opening 28 of the peripheral channel 25 comprise end fittings and form the means 7 for connection to an outer fluid flow circuit (not represented), so that the fluid enters the electrode through the central channel 21 and leaves it through the peripheral channel(s) 25. The reversed construction is also possible, that is to say that the connection means 7 comprise the inlet opening of the peripheral channel 25 and the outlet opening of the central channel 21, so that the fluid enters the electrode through the peripheral channel(s) 25 and leaves it through the central channel 21. The connection means 7 form a connector in one or two parts, assembled with each other by fitting and fixed on the tube 20 by gluing in the areas 9 so as to create the required tightness and close the peripheral channels 25, allowing to separate them hydraulically from the central channel 21 (see FIG. 3A), or by any equivalent means.

One of the peripheral channels 25 provided in the tube 20 delimits advantageously a sealed and insulated passage for the electrical power supply wires (not represented) of the contact pads 3, and these wires may be overmolded with an electrically insulating synthetic material. In an embodiment variant, the electrical wires may be formed by physical vacuum deposition of metal (PVD) or by any equivalent process.

Figure 2:
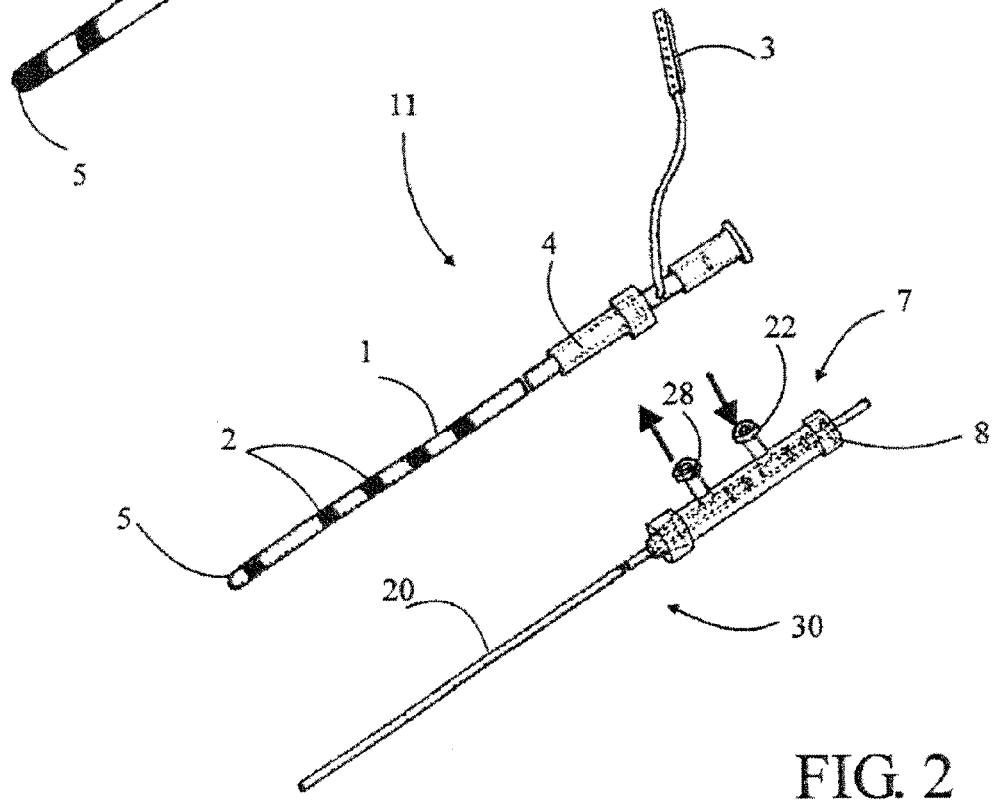
FIG. 2 is a side view of an embodiment variant of the intracerebral electrode according to the invention, in two parts.

In the embodiment of FIG. 1, the tube 20 forms the body 1 of the electrode 10 while, in the variant of FIG. 2, the tube 20 forms a separate part 30 accommodated in the hollow body 1 of the electrode 11. The body 1 and/or the tube 20 is tightly closed by a threaded plug 8 or similar. This plug 8 may also be arranged to close the body 1 and/or the tube 20 after having created the vacuum. This plug can be inert or made of a contact pad. It can also be made of a reading prism for cellular imaging in vivo by confocal microscopy.

In all cases, the body 1 of the electrode 10 including the tube 20, or the body 1 of the electrode 11 and its associated tube 20, can be made out of materials permeable to magnetic radiation, such as polyamide, polyether block amide, polycarbonate, polytetrafluoroethylene (PTFE) or similar, in order to be able to perform the treatment under the control of a magnetic resonance imaging (MRI) system.

The electrode 10, 11 can comprise at least one side window (not represented) near its distal end 5, this window being transparent to laser radiation. This laser radiation is emitted by a fiber optic 6 introduced in the central channel 21 of the tube 20 and the end of which can comprise a reversed cone whose angle defines the shape of the beam and thus the shape of the thermolesion. The body 1 of the electrode 10, 11 can be made entirely out of a synthetic material transparent to laser radiation such as polyamide, polyether block amide, polycarbonate, polyimide, polytetrafluoroethylene or similar, and resisting to a temperature of at least 150° C. This embodiment allows doing without the side window and thus having more freedom for performing a laser radiation treatment on the whole length of the electrode 10, 11. The contact pads 2 are formed by lands or rings and may be glued or overmolded on the body 1 of the electrode 10, 11. In an embodiment variant, the contact pads 2 can be made by physical vacuum deposition of metal (PVD) or by any equivalent process. These contact pads 2 are located at a regular pitch, for example equal to 5 mm, or at an irregular pitch. They must be made out of materials permeable to magnetic radiation, such as titanium, titanium and nickel alloys, carbon graphite, cobalt-based alloys, tantalum, platinum and iridium alloys, copper, nickel and zinc-based nonferrous alloys, zamac, copper and beryllium alloys, or similar.

Possibilities For Industrial Application:

The difficulty in the design of the intracerebral electrodes 10 and 11 as described lies in their small diameter and in the arrangement of the fluid circuit in a very confined space. Only as an illustration, the outer diameter of the electrodes 10, 11 is for example comprised between 1.6 and 1.7 mm, the inner diameter of the central channel 21 is comprised between 0.8 and 0.9 mm, this channel being able to accommodate a fiber optic 6 or any other treatment instrument with a diameter comprised between 0.6 and 0.75 mm. These figures are only given as an illustration and are in no case limitative data.

These intracerebral electrodes 10, 11 allow the neurosurgeon to perform an operation in complete safety for the patient and limiting the interventions. One or several intracerebral electrodes 10, 11 are located on the head of a patient and connected to an electro-encephalogram (EEG) in order to monitor the brain activity of certain areas and detect, if the case arises, the epileptogenic area(s). As soon as an area is identified, the neurosurgeon can use the electrode(s) in place to perform his treatment. He introduces a fiber optic 6 in the central channel 21 of the electrode 10, 11 until he reaches the distal end 5. When the end of the fiber optic 6 reaches the stop, he pulls it back some millimeters in order to be in front of the side window 9, if it exists, or between two contact pads 3. Before carrying out the thermolesion, he connects the inlet 22 and outlet 28 openings of the inner fluid flow circuit to the outer fluid flow circuit in order to control the temperature of the electrode 10, 11. The fluid then flows in a closed loop, going down towards the distal end of the electrode 10, 11 through the central channel 21 around the fiber optic 6 than going back upwards through the peripheral channels 25, or vice-versa. During this time, the neurosurgeon carries out the thermolesion by controlling the electrical power supply of the fiber optic 6. The thermolesion will only require some seconds, or perhaps some minutes, depending of the depth of the lesion. After the treatment, he can check the treated area with the help of the electro-encephalogram, allowing him to make sure that the area has disappeared. Of course, the whole operation can be monitored by a magnetic resonance imaging (MRI) system.

This description shows clearly that the invention allows reaching the goals defined. The present invention is not restricted to the examples of embodiment described, but extends to any modification and variant which is obvious to a person skilled in the art while remaining within the scope of the protection defined in the attached claims.

The invention claimed is:

1. An intracerebral electrode (10, 11) comprising:
   a narrow, elongated body (1) for being implanted in the brain of a patient, and the elongated body (1) being provided with contact pads (2) that are electrically connected to a measuring apparatus for monitoring electric brain activity of the patient,
   a mounting member (4) for attaching the body to a head of a patient,
   the electrode body being hollow for receiving a treatment instrument (6) to create a thermolesion of a targeted cerebral area, and being provided with a closed distal end (5), and
   the electrode body comprising a closed inner fluid flow circuit (20), provided inside the electrode body (1) up to an area adjacent the closed distal end (5),
   wherein the closed inner fluid flow circuit comprises a hollow tube (20) that delimits a central channel (21) provided with at least one inlet opening (22) and one outlet opening (23), and fluid flows longitudinally through the central channel (21)
   the treatment instrument (6) is introduced in the central channel (21),
   a wall of the hollow tube (20) comprises a double wall (24) that delimits at least one peripheral channel (25) provided with at least one inlet opening (27) and one outlet opening (28),
   the central channel (21) and the peripheral channel (25) communicate with each other through the outlet opening (23) of one of the channels (21) and the inlet opening (27) of the other channel (25),
   the electrode comprises connection means (7) located outside the electrode body comprising a closed inner fluid flow circuit (20), provided inside the electrode body (1), and includes the inlet opening (22) of the central channel (21) and the outlet opening (28) of the peripheral channel (25) so as to connect the closed inner fluid flow circuit to an outer fluid flow circuit so that the fluid, moved along the outer fluid flow circuit, flows into the electrode through the inner circuit in order to control dissipation of heat or cold of the electrode and prevent any collateral damage due to a treatment with the help of the treatment instrument.

2. The electrode according to claim 1, wherein the tube (20) forms the electrode body (1) of the electrode (10).

3. The electrode according to claim 1, wherein the tube (20) forms a separate part (30) accommodated within the hollow body (1) of the electrode (11).

4. The electrode according to claim 1, wherein the tube (20) comprises at least first and second peripheral channels (25), the first peripheral channels belongs to the inner fluid flow circuit while the second peripheral channel delimits a sealed and insulated passage for electrical power supply wires of the contact pads (2).

5. The electrode according to claim 1, wherein at least one of the electrode body (1) and the tube (20) is manufactured from a material permeable to magnetic radiation.

6. The electrode according to claim 5, wherein the material permeable to magnetic radiation is selected from the group consisting of polyamide, polyether block amide, polycarbonate, polyimide and polytetrafluoroethylene.

7. The electrode according to claim 1, wherein at least one of the electrode body (1) and the tube (20) are at least partially transparent to laser radiation.

8. The electrode according to claim 1, wherein the electrode comprises a plug (8) arranged to close, in a fluid tight manner, at least one of the electrode body (1) and the tube (20).

9. The electrode according to claim 8, wherein the plug (8) is arranged to close at least one of the electrode body (1) and the tube (20) under vacuum.

10. The electrode according to claim 1, wherein the electrode comprises at least one side radiation window, adjacent a distal end (5) thereof, which is transparent to a laser.

11. The electrode according to claim 1, wherein the contact pads (2) are one of overmolded on and glued to the electrode body (1) of the electrode (10, 11).

12. The electrode according to claim 11, wherein the contact pads (3) are manufactured from of a material permeable to magnetic radiation.

13. The electrode according to claim 12, wherein the material permeable to magnetic radiation is selected from the group consisting of titanium, titanium and nickel alloys, carbon graphite, cobalt-based alloys, tantalum, platinum and iridium alloys, copper, nickel and zinc-based nonferrous alloys, zamac, copper and beryllium alloys.

14. The electrode according to claim 1, wherein at least one of the contact pads (2) and the electrical power supply wires are formed by vacuum deposition of metal.

15. The electrode according to claim 1, wherein the treatment instrument (6) is a fiber optic that emits laser radiation.

16. The electrode according to claim 1, wherein the treatment instrument (6) is a fiber optic with a reversed cone on a distal end, the reversed cone defining a shape of a laser beam emitted through the fiber optic and thus a shape of the thermolesion.

17. The electrode according to claim 1, wherein the treatment instrument (6) is a fiber optic that is inserted into the central channel and is in fluid communication with fluid flowing through the central channel.

18. An intracerebral electrode (10, 11) comprising:
a narrow, elongate electrode body being implantable in a brain of a patient, the elongate body comprising contact pads that are electrically connected to an electro-encephalogram to measure electrical activity of the brain of the patient;
a mounting member that attaches the electrode body to a head of a patient;
the electrode body comprises a cylindrical wall that has an open end and a closed distal end, the cylindrical wall defines a central channel, the open end of the cylindrical wall receives a treatment instrument, which creates a thermolesion of a targeted cerebral area that extends through the central channel to adjacent the closed distal end of the cylindrical wall, the cylindrical wall comprises at least one peripheral channel that extends along the cylindrical wall from adjacent the open end to adjacent the distal end;
the at least one peripheral channel has an inlet opening located adjacent the distal end of the cylindrical wall and an outlet opening located adjacent the open end of the cylindrical wall, the inlet opening of the at least one peripheral channel communicates with the central channel at the distal end of the cylindrical wall to facilitate a flow of fluid from the open end of the cylindrical wall longitudinally through the central channel to the distal end of the cylindrical wall and through the inlet opening of the at least one peripheral channel to the outlet opening of the at least one peripheral channel, the flow of fluid defining a closed inner fluid flow circuit within the electrode body;
the open end of the cylindrical wall of the electrode body is received within a connection means and communicates with an inlet of the connection means and the outlet opening of the peripheral channel communicates with an outlet of the connection means such that the inner fluid flow circuit connects to an outer fluid flow circuit; and
fluid flows in the inner fluid flow circuit to control dissipation of heat or cold of the intracerebral electrode and to prevent any collateral damage due to a treatment with the help of the treatment instrument.

19. An intracerebral electrode (10, 11) comprising:
a narrow, elongated body (1) for being implanted in the brain of a patient, and the elongated body (1) being provided with contact pads (2) that are electrically connected to a measuring apparatus,
a mounting member (4) for attaching the body to a head of a patient,
the electrode body being hollow for receiving a treatment instrument (6) and being provided with a closed distal end (5), and
the electrode body comprising a closed inner fluid flow circuit (20), provided inside the electrode body (1) up to an area adjacent the closed distal end (5),
wherein the closed inner fluid flow circuit comprises a hollow tube (20) that delimits a central channel (21) provided with at least one inlet opening (22) and one outlet opening (23), the central channel is aligned radially centrally with the elongated body (1), and fluid flows longitudinally through the central channel,
the treatment instrument (6) is introduced in the central channel (21),
a wall of the hollow tube (20) comprises a double wall (24) that delimits at least one radially offset peripheral channel (25) provided with at least one inlet opening (27) and one outlet opening (28), and the at least one peripheral channel substantially surrounds the central channel,
the central channel (21) and the at least one peripheral channel (25) communicate with each other through the outlet opening (23) of one of the central and the peripheral channels (21) and the inlet opening (27) of the other of the central and the peripheral channel (25), and
the electrode comprises connection means (7) located outside the electrode body comprising a closed inner fluid flow circuit (20), provided inside the electrode body (1), and includes the inlet opening (22) of the central channel (21) through which fluid one of enters and exits the electrode body, and the outlet opening (28) of the peripheral channel (25) through which fluid the other of enters and exits the electrode body, so as to connect the closed inner fluid flow circuit to an outer fluid flow circuit so that the fluid, moved along the outer fluid flow circuit, flows into the electrode through the inner circuit in order to control dissipation of heat or cold of the electrode and prevent any collateral damage due to a treatment with the help of the treatment instrument.

20. The electrode according to claim 19 wherein the central channel (21) and the peripheral channel (25) extend longitudinally along a majority of a length of the elongate body (1), the at least one peripheral channel comprises a plurality of peripheral channels, and the plurality of peripheral channels substantially surround the central channel.

* * * * *